United States Patent
Kato

(10) Patent No.: US 10,363,406 B2
(45) Date of Patent: Jul. 30, 2019

(54) METHOD FOR PRODUCING ACICULAR BODY

(71) Applicant: TOPPAN PRINTING CO., LTD., Taito-ku (JP)

(72) Inventor: Hiroyuki Kato, Taito-ku (JP)

(73) Assignee: TOPPAN PRINTING CO., LTD., Taito-ku (JP)

( * ) Notice: Subject to any disclaimer, the term of this patent is extended or adjusted under 35 U.S.C. 154(b) by 577 days.

(21) Appl. No.: 14/922,970

(22) Filed: Oct. 26, 2015

(65) Prior Publication Data

US 2016/0038729 A1 Feb. 11, 2016

Related U.S. Application Data

(63) Continuation of application No. PCT/JP2014/061373, filed on Apr. 23, 2014.

(30) Foreign Application Priority Data

Apr. 26, 2013 (JP) ................................. 2013-093572

(51) Int. Cl.
*A61M 37/00* (2006.01)
*B29C 41/12* (2006.01)
(Continued)

(52) U.S. Cl.
CPC ....... *A61M 37/0015* (2013.01); *B29C 39/026* (2013.01); *B29C 41/12* (2013.01);
(Continued)

(58) Field of Classification Search
None
See application file for complete search history.

(56) References Cited

U.S. PATENT DOCUMENTS 3,814,097 A  6/1974 Ganderton et al.
2008/0200883 A1* 8/2008 Tomono ............ A61M 37/0015
604/272

(Continued)

FOREIGN PATENT DOCUMENTS

JP   48-93192 A   12/1973
JP   2008-6178 A   1/2008
(Continued)

OTHER PUBLICATIONS

International Search Report dated Jul. 29, 2014 in PCT/JP2014/061373, filed Apr. 23, 2014.
(Continued)

*Primary Examiner* — Seyed Masoud Malekzadeh
*Assistant Examiner* — Manley L Cummins, IV
(74) *Attorney, Agent, or Firm* — Oblon, McClelland, Maier & Neustadt, L.L.P.

(57) ABSTRACT

A method for producing an acicular body having a support base and an acicular protrusion on one surface of the support base includes supplying an acicular body-forming liquid, in which an acicular body-forming material is dissolved or dispersed in a solvent, to an intaglio plate having a recess corresponding to a protrusion, under a first pressure environment of not more than 0.05 MPa, changing the first pressure environment of the acicular body-forming liquid supplied to the intaglio plate to a second pressure environment of higher than 0.05 MPa, drying the acicular body-forming liquid supplied to the intaglio plate such that an acicular body is formed, and peeling the acicular body from the intaglio plate.

20 Claims, 11 Drawing Sheets

(51) Int. Cl.
*B29C 39/02* (2006.01)
*B29C 41/36* (2006.01)
*B29C 41/50* (2006.01)
*B29L 31/00* (2006.01)

(52) U.S. Cl.
CPC .............. *B29C 41/36* (2013.01); *B29C 41/50* (2013.01); *A61M 2037/0046* (2013.01); *A61M 2037/0053* (2013.01); *B29L 2031/753* (2013.01); *B29L 2031/756* (2013.01)

(56) References Cited

U.S. PATENT DOCUMENTS

| | | | | |
|---|---|---|---|---|
| 2009/0143749 | A1* | 6/2009 | Sugimura | A61M 37/0015 604/272 |
| 2009/0234301 | A1* | 9/2009 | Tomono | A61M 37/0015 604/272 |
| 2010/0185162 | A1* | 7/2010 | Shiomitsu | A61M 37/0015 604/272 |
| 2011/0192562 | A1* | 8/2011 | Motoi | A61M 37/0015 163/5 |

FOREIGN PATENT DOCUMENTS

| | | |
|---|---|---|
| JP | 2009-233170 A | 10/2009 |
| JP | 2010-94414 A | 4/2010 |
| JP | 2011-78617 A | 4/2011 |
| WO | WO 2008/004597 | 1/2008 |
| WO | WO 2008/013282 | 1/2008 |
| WO | WO 2006/020632 | 2/2008 |
| WO | WO 2008/062832 A1 | 5/2008 |

OTHER PUBLICATIONS

Office Action dated Oct. 10, 2017 in Japanese Patent Application No. 2015-513785 (with English language translation).

* cited by examiner

METHOD FOR PRODUCING ACICULAR BODY

CROSS-REFERENCE TO RELATED APPLICATIONS

The present application is a continuation of International Application No. PCT/JP2014/061373, filed Apr. 23, 2014, which is based upon and claims the benefits of priority to Japanese Application No. 2013-093572, filed Apr. 26, 2013. The entire contents of these applications are incorporated herein by reference.

BACKGROUND OF THE INVENTION

Field of the Invention

The present invention relates to a method for producing an acicular body.

Discussion of the Background

A transdermal absorption method is used for administering a substance, such as a drug, to be delivered into a body by having the substance penetrated into the body from the skin. With this method, a substance to be delivered can be easily administered without causing pain to the human body.

In the field of transdermal administration, there is proposed a method in which a drug or the like is administered into the skin by using an acicular body, in which a micrometer scale needle is formed, to pierce the skin (refer to PTL 1).

As a method for producing the acicular body, there is proposed a method according to which an original plate is prepared using machine processing, the original plate is used for forming a transfer plate, and the transfer plate is used for performing transfer molding (refer to PTL 2).

Furthermore, as a method for producing the acicular body, there is proposed a method according to which an original plate is prepared using an etching process, the original plate is used for forming a transfer plate, and the transfer plate is used for performing transfer molding (refer to PTL 3).

The material composing the acicular body is preferably a material that does not adversely affect the human body, in the event that a broken piece of the acicular body has remained in the human body. Therefore, a biocompatible material, such as chitosan, is proposed as an acicular body-forming material (refer to PTL 4).

PTL 1: JP-A-S48-093192
PTL 2: WO 2008/013282
PTL 3: WO 2008/004597
PTL 4: WO 2008/020632

SUMMARY OF THE INVENTION

According to one aspect of the present invention, a method for producing an acicular body having a support base and an acicular protrusion on one surface of the support base includes supplying an acicular body-forming liquid, in which an acicular body-forming material is dissolved or dispersed in a solvent, to an intaglio plate having a recess corresponding to a protrusion, under a first pressure environment of not more than 0.05 MPa, changing the first pressure environment of the acicular body-forming liquid supplied to the intaglio plate to a second pressure environment of higher than 0.05 MPa, drying the acicular body-forming liquid supplied to the intaglio plate such that an acicular body is formed, and peeling the acicular body from the intaglio plate.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
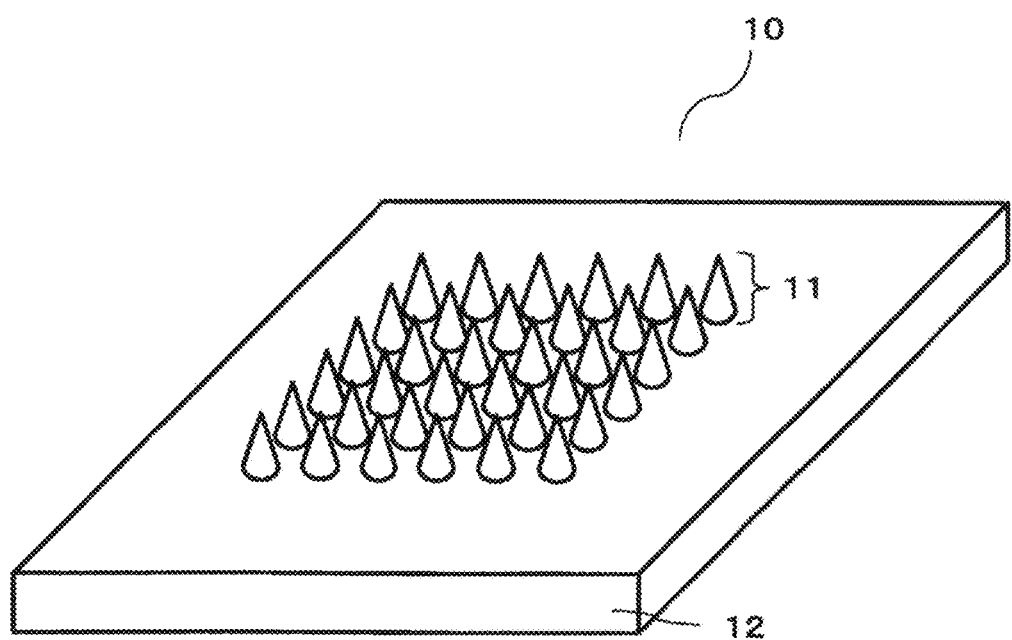
FIG. 1 is a perspective view of an acicular body of the present invention.

The embodiments will now be described with reference to the accompanying drawings, wherein like reference numerals designate corresponding or identical elements throughout the various drawings.

An acicular body of the present invention will be described.

FIG. 1 shows a perspective view of the acicular body of the present invention. An acicular body 10 of the present invention is provided with acicular protrusions 11 on a support base 12.

Each of the acicular protrusions 11 of the acicular body of the present invention pierces the skin. In the acicular body of the present invention, each protrusion 11 is merely required to have a shape that is suitable for piercing the skin. The protrusion 11 has, for example, a circular conical shape, a pyramid shape, a circular columnar shape, a prismatic shape, or a pencil shape (having a columnar body and a conical tip). The protrusion may be in a mode (1) where a single protrusion is present on the support base, or in a mode (2) where a plurality of protrusions are closely set up on the support base. When a plurality of protrusions are closely set up on the support base, the protrusions are preferably arranged in an array. The term "in an array" refers to a state in which acicular body units are orderly arranged. For example, the array includes a grid array, a closest-packing array, a concentric array, and a random array.

In a mode of usage of the acicular body of the present invention, an applicator may be mounted to fix the insertion position and direction of the acicular body. In the acicular body of the present invention, holes may be provided to respective protrusions. Each hole may or may not pass through the back surface of the support base. Alternatively, the support base may be provided with holes. Each hole may or may not pass through the back surface of the support base.

Figure 2A:
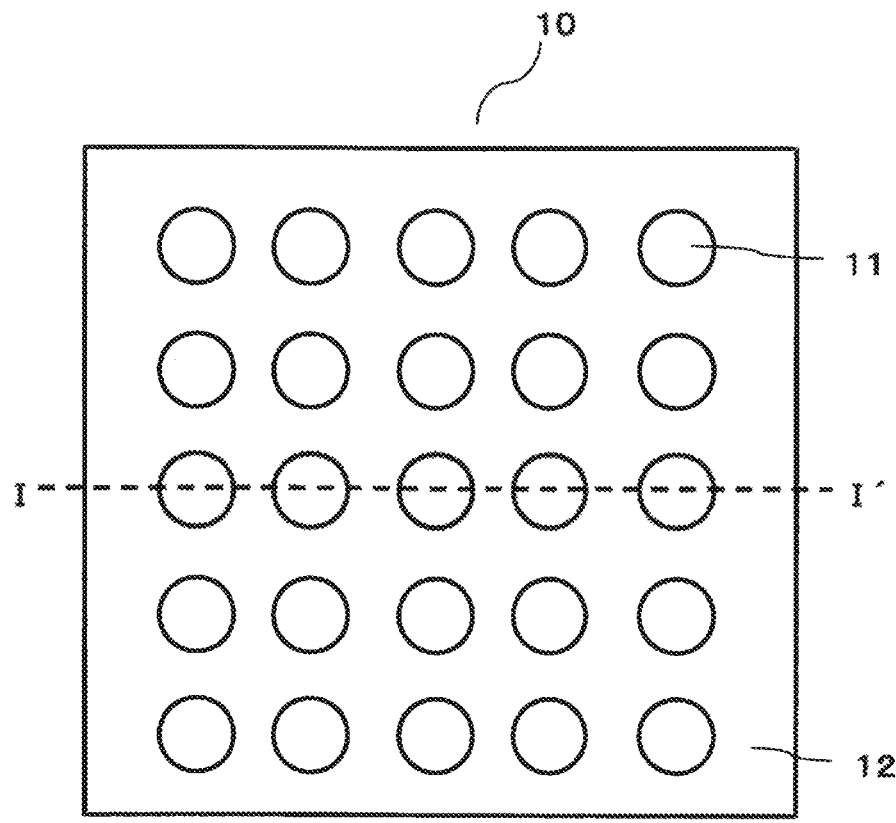
FIGS. 2(a) and 2(b) are schematic top and cross-sectional views of the acicular body of the present invention.
Figure 2B:
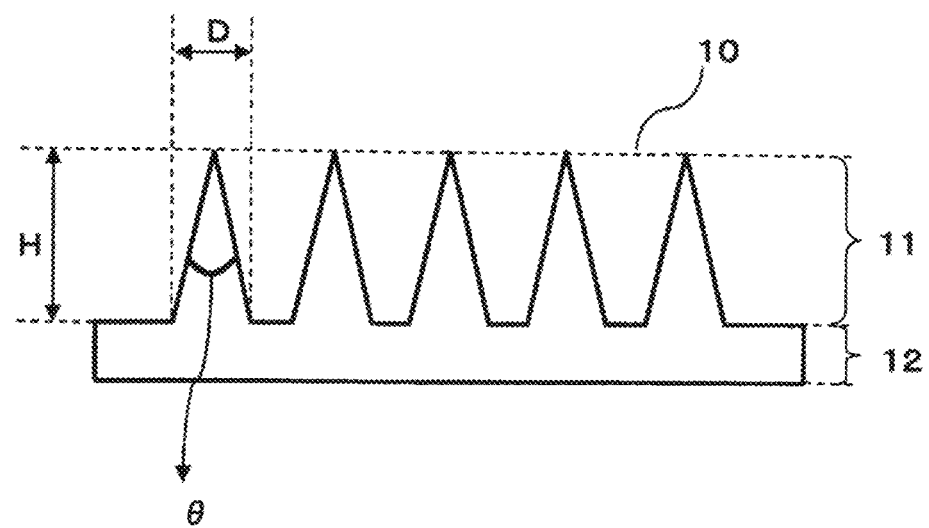

FIGS. 2(a) and 2(b) show schematic diagrams of the acicular body of the present invention. FIG. 2(a) shows a top view as viewed from the protrusion side of the acicular body. FIG. 2(b) shows a cross-sectional view taken along the I-I' plane of the acicular body of FIG. 2(a).

In the acicular body 10 of the present invention, from a dimensional viewpoint, each acicular protrusion 11 preferably has a narrowness and a height suitable for forming a piercing hole in the skin. Specifically, each protrusion 11 shown in FIG. 2 preferably has a height H ranging from 10 μm to 1000 μm inclusive. The height H of the protrusion corresponds to the distance from the support base 12 to the tip of the protrusion 11.

The height H of the protrusion is preferably determined in the range mentioned above, taking account of the extent of the depth inside the skin by which the piercing hole should be formed when the skin is pierced with the acicular body.

In particular, when the piercing hole formed by piercing the acicular body should be within the cornified layer, for example, it is desirable that the height H of the acicular protrusion is within the range of 10 μm to 300 μm, and more preferably within the range of 30 μm to 200 μm.

When the piercing hole formed by piercing the acicular body should have the length of passing through the cornified layer but not reaching the nervous layer, it is desirable that the height H of the acicular protrusion is within the range of 200 μm to 700 μm, more preferably within the range of 200 μm to 500 μm, and still more preferably within the range of 200 μm to 300 μm.

When the piercing hole formed by piercing the acicular body should have the length of reaching the dermis, the height H of the acicular protrusion is preferably within the range of 200 μm to 500 μm. When the piercing hole formed by piercing the acicular body should have the length of reaching the epidermis, the height H of the acicular protrusion is preferably within the range of 200 μm to 300 μm.

Each protrusion preferably has a width D ranging from 1 μm to 300 μm. The width D of the protrusion is preferably determined in the range mentioned above, taking account, for example, of the extent of the depth inside the skin by which the piercing hole should be formed when the skin is pierced with the acicular body.

The width D of the protrusion is the maximum length of the protrusion that is in contact with the support base, when the protrusion is projected in parallel with the base surface. For example, when the protrusion has a circular conical shape, the diameter of the circle on the plane on which the protrusion and the support base come into contact is set as the width D. When the protrusion has a square conical shape, the diagonal line of the square on the plane on which the protrusion and the support base come into contact is set as the width D. When the protrusion has a circular columnar shape, the diameter of the circle on the plane on which the protrusion and the support base come into contact is set as the width D. When the protrusion has a square columnar shape, the diagonal line of the square on the plane on which the protrusion and the support base come into contact is set as the width D.

The aspect ratio is preferably within the range of 1 to 10. Using the length H and width D of the protrusion, an aspect ratio A is defined as A=H/D.

In the acicular body according to an embodiment, when each protrusion has a point angle, as in a conical shape, and is permitted to penetrate the cornified layer, the protrusion desirably has a point angle θ ranging from 5° to 30°, and more preferably ranging from 10° to 20°. The point angle θ refers to a maximum angle that is an angle (apex angle) when the protrusion is projected in parallel with the support base surface.

In the acicular body according to the embodiment, the support base is preferably made of the same material as that of the protrusions. When the support base is made of the same material as that of the protrusions, the support base and the protrusions can be integrally molded.

The support base may have a multi-layer structure in which a material other than the material of the protrusions is laminated as a bottom layer. When several materials are laminated, the support base can take advantages of the physical properties of the materials, as described below.

(1) A support base can be bent into a roll shape if the base includes an upper layer made of the same material as that of the protrusions, with the protrusions being formed thereon, and includes a bottom layer made of a highly flexible material.

(2) A support base can be bent into a roll shape if the base includes an upper layer made of a material having greater ductility than that of a bottom layer.

(3) A support base can also be bent into a roll shape if the base includes an upper layer made of a material having lower shrinkage than that of a bottom layer.

(4) A support base can reduce damage to the protrusions of an acicular body when two or more acicular bodies are stored in a stack, with the base each including a bottommost layer made of a material having flexibility.

In the acicular body of the present invention, at least the protrusions are preferably made of a water-soluble polymer or polysaccharide. The acicular body-forming material preferably contains a water-soluble polymer or polysaccharide.

The water-soluble polymers and polysaccharides that can be used include chitosan, chitosan succinamide, hydroxypropyl cellulose (HPC), carboxymethyl cellulose (CMC), sodium chondroitin sulfate, curdlan, trehalose, sucrose, gelatin, collagen, pullulan, pectin, alginate, starch, methyl cellulose, hydroxypropyl methylcellulose (HPMC), polyvinyl alcohol (PVA), polyacrylate-based polymers, polyacrylamide (PAM), polyethylene oxide (PEO), and the like. However, the water-soluble polymers and polysaccharides are not limited to these materials. These materials may be used in combination.

Among these materials, the acicular body-forming material is preferably selected from chitosan, chitosan succinamide, hydroxypropyl cellulose, carboxymethyl cellulose, sodium chondroitin sulfate, curdlan, trehalose, sucrose, gelatin, collagen, pullulan, pectin, and alginate. The reason for this is that biological safety is high. These materials may be used in combination.

The acicular body-forming material of the present invention is not particularly limited as far as the material can dissolve or disperse the acicular body in a solvent, and can be provided as a liquid substance (acicular body-forming liquid).

In an acicular body production method of the present invention, the acicular body may be produced by permitting the acicular body-forming material to contain a substance to be delivered into the skin. The substance to be delivered can include a pharmacologically active substance or a cosmetic substance. In this case, when a material having fragrance is the substance to be delivered, the substance to be delivered can emit a scent during use. Thus, an acicular body can be provided that is preferably used as a beauty product.

The pharmacologically active substance may be selected as appropriate depending on usage. For example, the pharmacologically active substance may be a vaccine such as for influenza, a pain-relief drug for cancer patients, insulin, biologics, a gene therapy drug, an injectable drug, an oral drug, or a dermatological drug product. Since the acicular body of the present invention pierces the skin, the acicular body can be applied to pharmacologically active substances that are required to be subcutaneously injected, besides the pharmacologically active substances used for conventional transdermal administration. In particular, administration of a vaccine or the like, which is an injectable agent, is painless when the acicular body is used. Therefore, the acicular body is suitable for children. In addition, children have difficulty in swallowing an oral drug in a conventional way of administration. However, when the acicular body is used, a drug is not required to be swallowed when administered. Therefore, the acicular body can be well applied to children.

The cosmetic substance to be delivered mentioned above is a composition used as cosmetics or beauty products. For example, the cosmetic substance to be delivered includes moisturizing agents, coloring materials, fragrances, and physiologically active substances that exhibit beauty effects (beneficial effects for wrinkles, acne, stretch marks, and the like, as well as beneficial effects for psilosis).

Hereinafter is described a first embodiment of the method for producing an acicular body of the present invention.

FIGS. 3(a)-5(b) show explanatory diagrams of the first embodiment of the method for producing an acicular body of the present invention. The method for producing an acicular body of the present invention (first embodiment) includes the following steps.

<Supplying Step>

A step of supplying an acicular body-forming liquid, in which the acicular body-forming material is dissolved or dispersed in a solvent, to an intaglio plate provided with recesses corresponding to the protrusions, under a pressure environment of not more than 0.05 MPa.

<Pressure Changing Step>

A step of changing the pressure environment for the acicular body-forming liquid supplied to the intaglio plate to a pressure environment in which the pressure is higher than 0.05 MPa.

<Drying Step>

A step of drying the acicular body-forming liquid in the intaglio plate and forming an acicular body.

<Peeling Step>

A peeling step of peeling the acicular body-forming liquid from the intaglio plate.

The following description sets forth in detail the supplying step, the pressure changing step, the drying step, and the peeling step of the method for producing an acicular body of the present invention (first embodiment).

<Supplying Step>

Figure 3A:
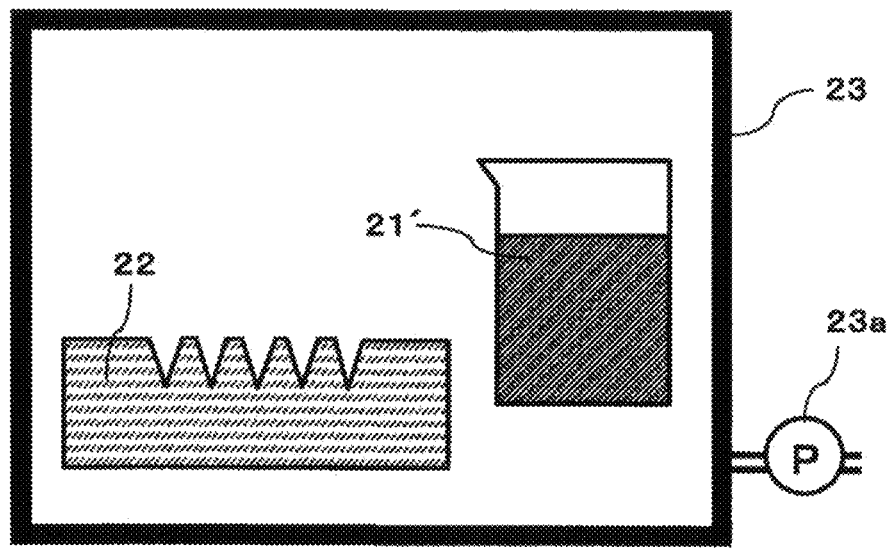
FIGS. 3(a) and 3(b) are explanatory diagrams (1) of a first embodiment of a method for producing the acicular body of the present invention.
Figure 3B:
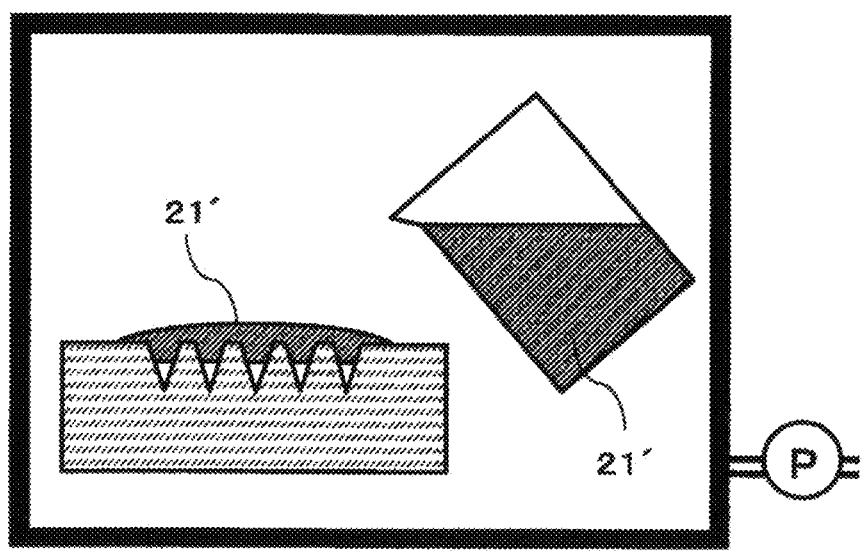
Figure 4A:
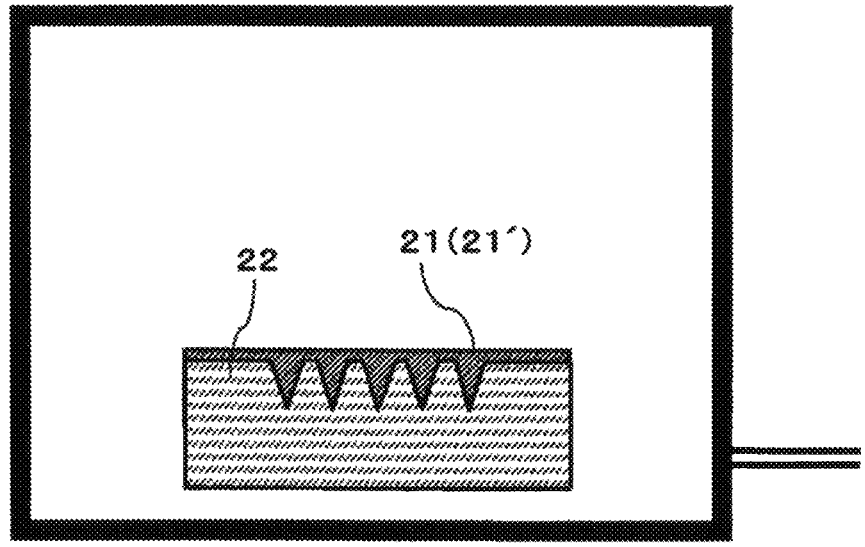
FIGS. 4(a) and 4(b) are explanatory diagrams (2) of the first embodiment of the method for producing the acicular body of the present invention.
Figure 4B:
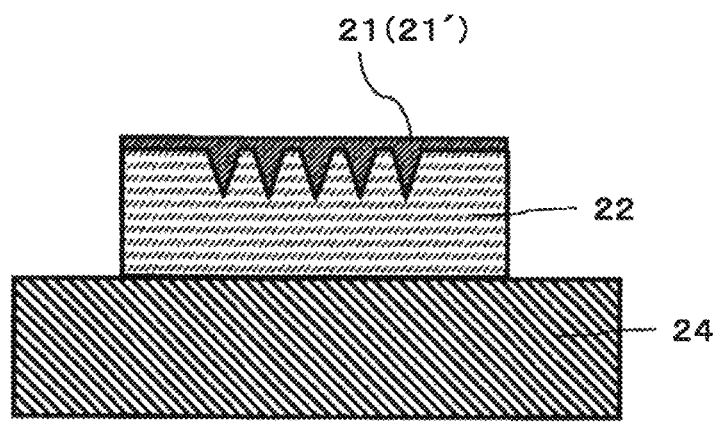

An acicular body-forming liquid 21', in which an acicular body-forming material is dissolved or dispersed in a solvent, and an intaglio plate 22 are arranged inside a vacuum chamber 23 (FIG. 3(a)). The vacuum chamber 23 is connected to a pump 23a and vacuum-drawn. Then, a pressure environment of not more than 0.05 MPa is created in the interior of the vacuum chamber 23, followed by supplying the acicular body-forming liquid 21' to the intaglio plate 22 (FIG. 3(b)). The intaglio plate is provided with recesses that correspond to the protrusions. The intaglio plate 22 may also be provided with a bank (protrusion) on the peripheral edge portion to control the wet spread of the acicular body-forming liquid over the intaglio plate.

The acicular body-forming liquid supplied to the intaglio plate is prepared by dissolving or dispersing the acicular body-forming material in a solvent, such as water. In this case, a substance to be delivered, such as a pharmacologically active substance or a cosmetic substance, may be mixed with the acicular body-forming liquid to have the substance contained in the acicular body to be produced. In addition, a dissolution enhancing substance may be added to the acicular body-forming liquid to dissolve the water-soluble polymer, i.e. the acicular body-forming material, into water, i.e. the solvent. For example, when chitosan is used, an acid is required to be added to the acicular body-forming liquid. The acicular body-forming liquid preferably has fluidity to an extent that the acicular body-forming liquid can flow into the intaglio plate. Preferably, the acicular body-forming liquid is subjected to defoaming treatment in advance. The defoaming treatment can be performed by storing the acicular body-forming liquid under a reduced pressure environment.

Preferably, the acicular body-forming liquid of the present invention has a viscosity ranging from 0.01 Pa·s to 100 Pa·s. In the method for producing an acicular body of the present invention, the acicular body-forming liquid can be filled well into the pointed bottom ends of the recesses of the intaglio plate, in using an acicular body-forming liquid having high viscosity ranging from 0.01 Pa·s to 100 Pa·s. That is, the method for producing an acicular body of the present invention is very highly effective, in using an acicular body-forming liquid having high viscosity ranging from 0.01 Pa·s to 100 Pa·s inclusive.

The following description deals with a method for producing an intaglio plate provided with recesses that correspond to the respective protrusions of the acicular body. An original plate that determines the shape of the acicular body is prepared, and then an intaglio plate is prepared from the original plate, with protrusions and recesses being inverted for the desired shape of an acicular body. The original plate that determines the shape of the acicular body can be produced by a known method according to the shape of the acicular body. The original plate may be formed using a microfabrication technique. The microfabrication technique includes, for example, lithography, wet etching, dry etching, sandblasting, laser machining, and precision machining. The intaglio plate can be formed from the original plate using a known feature replication method. For example, (1) a Ni-based intaglio plate can be formed by Ni-electrocasting, or (2) a resin-based intaglio plate can be transfer-molded using a molten resin, such as silicone resin.

In the method for producing an acicular body of the present invention, the acicular body-forming liquid 21' is supplied to the intaglio plate 22 under a reduced pressure environment. Specifically, the intaglio plate is placed inside the vacuum chamber. Then, after creating a reduced pressure environment in the vacuum chamber, the acicular body-forming liquid is supplied. The method for producing an acicular body of the present invention is characterized in that the acicular body-forming liquid is supplied in a pressure environment of not more than 0.05 MPa.

In the method for producing an acicular body of the present invention, it is preferable that the degree of vacuum in the reduced pressure environment is as low as possible, taking account of the suitability of the liquid to be filled in the tips of the protrusions, at the acicular body-forming liquid supplying step. However, when the degree of vacuum in the reduced pressure environment is too low, long time is taken before reaching the desired degree of vacuum and this may lead to a problem of increasing production cost. Thus, in the method for producing an acicular body of the present invention, it is preferable that the acicular body-forming liquid supplying step is performed under a pressure environment of 0.01 MPa to 0.05 MPa.

In the method for producing an acicular body of the present invention, the following method is preferably used for supplying the acicular body-forming liquid to the intaglio plate. Specifically, in the method, a container provided with an opening in the top face is arranged inside the vacuum chamber as in FIGS. 3(a) and 3(b), and the container is tilted to drip and supply the acicular body-forming liquid from the opening to the intaglio plate.

<Pressure Changing Step>

Then, the pressure environment for the acicular body-forming liquid supplied to the intaglio plate is changed to one in which the pressure higher than 0.05 MPa. In the present invention, the acicular body-forming liquid is supplied to the intaglio plate under a pressure environment of not more than 0.05 MPa, followed by changing the pressure environment to one in which the pressure is higher than at the supplying step. Thus, the acicular body-forming liquid supplied onto the intaglio plate is filled into the pointed bottom ends of the recesses of the intaglio plate (FIG. 4(a)).

In the method for producing an acicular body of the present invention, the acicular body-forming liquid is supplied to the intaglio plate under a pressure environment of not more than 0.05 MPa, followed by introducing air into the vacuum chamber to change the pressure environment at the drying step to one in which the pressure higher than at the supplying step but not more than the atmospheric pressure (0.1 MPa). Thus, the intaglio plate can be filled with the acicular body-forming liquid to the pointed bottom ends of the recesses. After that, the acicular body-forming liquid on the intaglio plate is dried and solidified, thereby preparing the acicular body filled the body-forming material to the tips of the protrusions.

In the present invention, preferably, the amount of pressure change at the pressure changing step is from 0.05 MPa to 0.1 MPa. When the amount of pressure change is less than 0.05 MPa, the degree of filling to the pointed bottom ends of the recesses may be lowered. Preferably, the amount of pressure change is as high as possible. However, when the amount of pressure change exceeds 1.0 MPa, production cost may increase.

In the method for producing an acicular body of the present invention, it is preferable that the pressure after pressure change at the pressure changing step is the atmospheric pressure, from the standpoint of manufacturing management.

<Drying Step>

Then, the acicular body-forming liquid supplied to the intaglio plate is dried and solidified to form the acicular body. Specifically, the atmospheric pressure (0.1 MPa) environment is created for the intaglio plate, and then the supplied acicular body-forming liquid 21' is located on a hot plate 24, followed by drying (FIG. 4(b)). To prevent air bubbles from remaining in the acicular body, the heating temperature is preferably set to a temperature at which the acicular body-forming liquid does not boil. Therefore, when water is used as the solvent for the acicular body-forming liquid, the heating temperature is preferably within the range of 40° C. to 90° C. Heating may be performed by any known heating means. Alternative to the method of using the hot plate, with the intaglio plate supplied with the acicular body-forming liquid being placed thereon, a method of using an oven can also be used, with the intaglio plate supplied with the acicular body-forming liquid being placed thereon. In addition, drying and solidification can also be performed at normal temperature without heating.

In the method for producing an acicular body of the present invention, it is preferable, from the standpoint of production cost, that after the acicular body-forming liquid is supplied to the intaglio plate under a pressure environment of not more than 0.05 MPa, the vacuum chamber is opened to atmospheric air to create the atmospheric pressure (0.1 MPa) in its interior, followed by drying the acicular body-forming liquid on the intaglio plate under the atmospheric pressure.

Alternatively, for example, the acicular body-forming liquid may be supplied to the intaglio plate, with a pressure environment of 0.04 MPa being created in the vacuum chamber. Then, air may be introduced into the vacuum chamber to create a pressure environment of 0.08 MPa, followed by drying and solidifying the acicular body-forming liquid on the intaglio plate under the pressure environment of 0.08 MPa.

Alternatively, for example, the acicular body-forming liquid may be supplied to the intaglio plate, with a pressure environment of 0.04 MPa being created in the vacuum chamber. Then, air may be introduced to the vacuum chamber to create a pressure environment of 0.08 MPa. After that, the pressure may be reduced again to 0.04 MPa, followed by drying and solidifying the acicular body-forming liquid on the intaglio plate under the pressure environment of 0.04 MPa.

<Peeling Step>

Figure 5A:
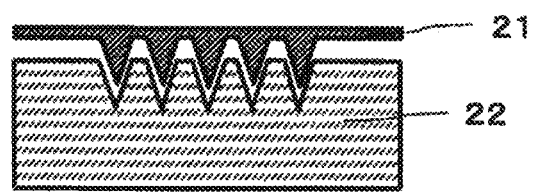
FIGS. 5(a) and 5(b) are explanatory diagrams (3) of the first embodiment of the method for producing the acicular body of the present invention.
Figure 5B:

Then, the acicular body 21 formed on the intaglio plate 22 is peeled off (FIG. 5(a)). As a peeling means, a known method of physically peeling the acicular body from the intaglio plate can be used. Alternatively, peeling can be performed using a chemical method, such as dissolving the intaglio plate. The acicular body is prepared as described above (FIG. 5(b)). After peeling, the outer edge portion of the acicular body can be punched to form a desired shape.

Hereinafter is described a second embodiment of the method for producing an acicular body of the present invention.

FIGS. 6(a)-9(c) show explanatory diagrams of the second embodiment of the method for producing an acicular body of the present invention. The method for producing an acicular body of the present invention (second embodiment) includes the following steps.

<Supplying Step>

A step of supplying an acicular body-forming liquid, in which an acicular body-forming material is dissolved or dispersed in a solvent, to an intaglio plate provided with recesses corresponding to the protrusions, under a pressure environment of not more than 0.05 MPa.

<Pressure Changing Step>

A step of changing the pressure environment for the acicular body-forming liquid supplied to the intaglio plate to a pressure environment higher than 0.05 MPa.

<Drying Step>

A step of drying the acicular body-forming liquid in the intaglio plate and forming the acicular body.

<Punching Step>

A step of punching the peripheral edge portion of the acicular body in the intaglio plate.

<Attaching Step>

A step of attaching an adhesive member on the surface of the acicular body from which the peripheral edge portion has been punched.

<Peeling Step>

A peeling step of peeling the acicular body fixed to the adhesive member from the intaglio plate.

The following description sets forth in detail the supplying step, the pressure changing step, the drying step, the punching step, the attaching step, and the peeling step of the method for producing the acicular body of the present invention (second embodiment).

<Supplying Step>

Figure 6A:
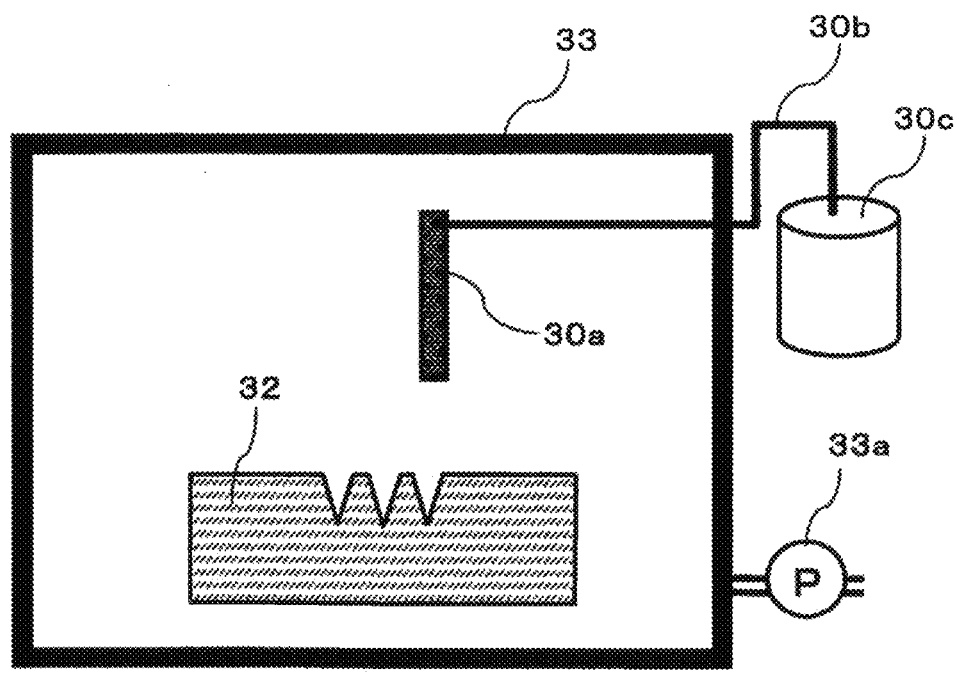
FIGS. 6(a) and 6(b) are explanatory diagrams (1) of a second embodiment of the method for producing the acicular body of the present invention.
Figure 6B:
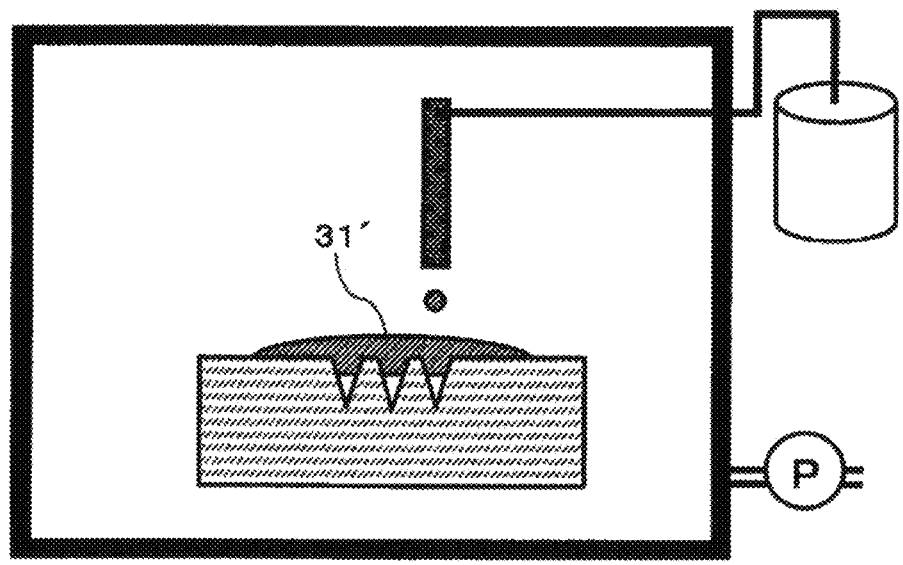
Figure 7A:
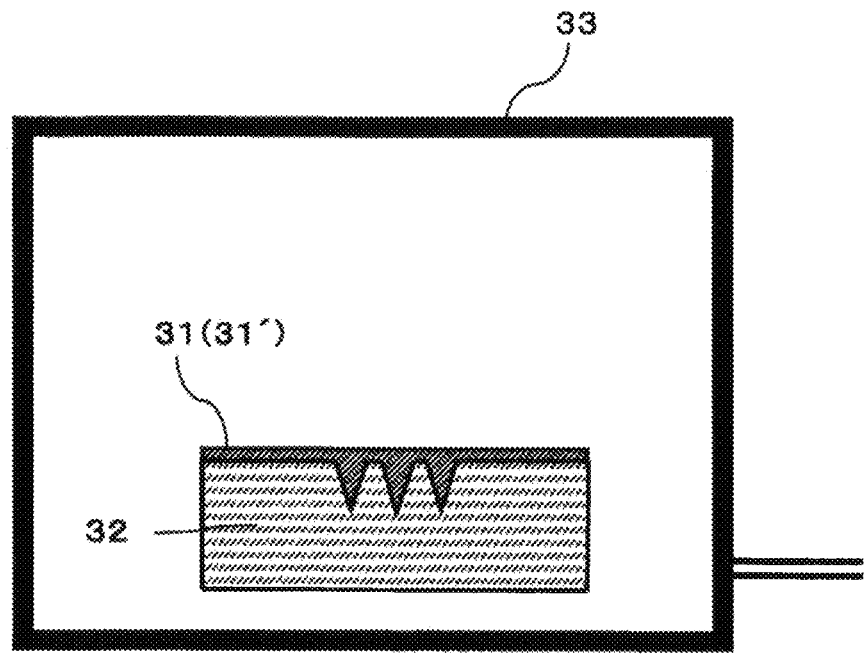
FIGS. 7(a) and 7(b) are explanatory diagrams (2) of the second embodiment of the method for producing the acicular body of the present invention.
Figure 7B:
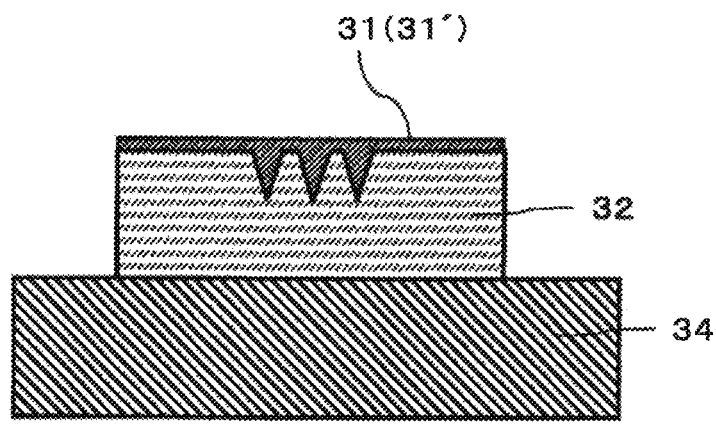

A nozzle 30a of a dispenser (quantitative liquid discharge device) and an intaglio plate 32 are arranged inside a vacuum chamber 33 (FIG. 6(a)). The nozzle 30a is used for discharging the acicular body-forming liquid in which an acicular body-forming material is dissolved or dispersed in a solvent. The vacuum chamber 33 is connected to a pump 33a and vacuum-drawn. Then, a pressure environment of not more than 0.05 MPa is created in the vacuum chamber 23, followed by supplying an acicular body-forming liquid 31' to the intaglio plate 32 (FIG. 6(b)). In the second embodiment, the dispenser (quantitative liquid discharge device) is provided as a supply mechanism. The dispenser includes the nozzle 30a for discharging the acicular body-forming liquid into the vacuum chamber 33, and also includes a tank 30c outside the vacuum chamber 33. The nozzle 30a and the tank 30c are connected to each other by a pipe 30b. In the method for producing an acicular body of the present invention, a method of tilting a container or a method of using a dispenser can be used at the acicular body-forming liquid supplying step.

<Pressure Changing Step>

The pressure changing step is the same as that of the first embodiment. The pressure environment for the acicular body-forming liquid supplied to the intaglio plate is changed to one in which the pressure is higher than 0.05 MPa (FIG. 7(a)). In the present invention, the acicular body-forming liquid is supplied to the intaglio plate under a pressure environment of not more than 0.05 MPa, and then the pressure environment is changed to one in which the pressure is higher than at the supplying step, thereby filling the acicular body-forming liquid supplied onto the intaglio plate into the pointed bottom ends of the recesses of the intaglio plate.

<Drying Step>

The drying step is the same as that of the first embodiment. The acicular body-forming liquid supplied onto the intaglio plate is dried and solidified to form the acicular body. After the intaglio plate is placed under the atmospheric pressure (0.1 MPa) environment, the supplied acicular body-forming liquid 31' is located on a hot plate 34, followed by drying (FIG. 7(b)). In the method for producing an acicular body of the present invention, the drying step is characterized in that the liquid is dried under a pressure environment in which the pressure is higher at the acicular body-forming liquid supplying step. Specifically, the acicular body-forming liquid is supplied to the intaglio plate under a pressure environment of not more than 0.05 MPa, and the pressure environment is changed to one in which the pressure is higher than at the supplying step. Thus, the acicular body-forming liquid supplied onto the intaglio plate is filled into the pointed bottom ends of the recesses of the intaglio plate.

<Punching Step>

Figure 8A:
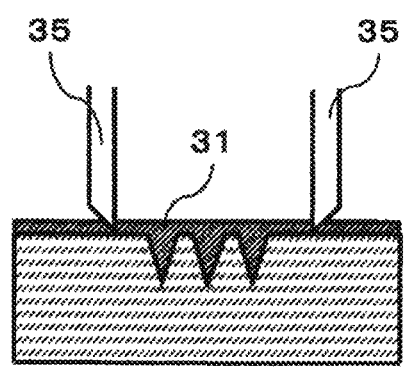
FIGS. 8(a) and 8(b) are explanatory diagrams (3) of the second embodiment of the method for producing the acicular body of the present invention.
Figure 8B:
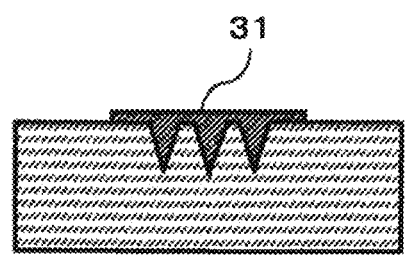

The solidified acicular body on the intaglio plate is punched to form a desired shape (FIGS. 8(a) and 8(b)). The acicular body can be punched using a punching blade, such as the Thomson blade 35. The acicular body can be punched together with the intaglio plate.

<Attaching Step>

Figure 9A:
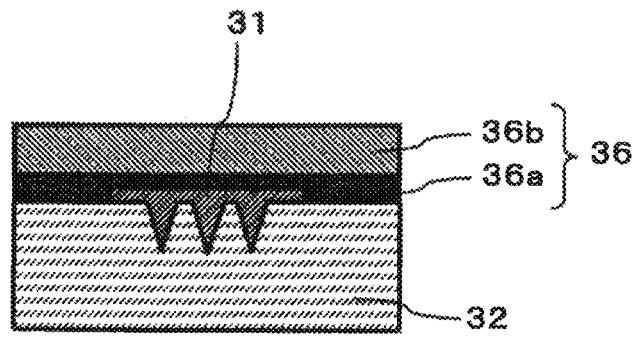
FIGS. 9(a), 9(b) and 9(c) are explanatory diagrams (4) of the second embodiment of the method for producing the acicular body of the present invention.

Then, an adhesive member 36 is attached to the back surface of the punched acicular body (FIG. 9(a)). The adhesive member includes an adhesive layer 36a provided on a film-shape base 36b. Preferably, an adhesive layer suitable for attachment to the skin is used in the adhesive member. An adhesive member that can endure a sterilizing step may be used.

<Peeling Step>

Figure 9B:
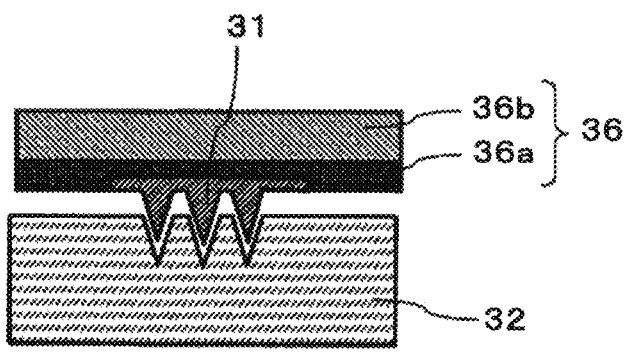
Figure 9C:
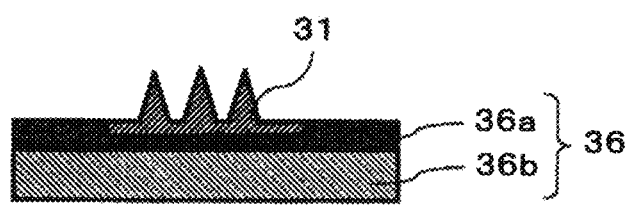

Then, the acicular body 31 formed on the intaglio plate 32 is peeled off (FIG. 9(b)). The acicular body 31 in a state of being fixed to the adhesive member 36, is peeled off integrally with the adhesive member 36. As the peeling means, a known mechanical peeling method can be used. Since the surface of the acicular body opposite to the protrusion-formed surface is fixed to the adhesive layer 26a of the adhesive member 36, peeling can be facilitated. The acicular body with an adhesive member 36 is prepared as described above (FIG. 9(c)). The acicular body with an adhesive layer can be directly fixed to the skin in a piercing state.

Through the use of the method for producing an acicular body of the present invention, the forming liquid can be filled into the pointed bottom ends of the recesses without forming air bubbles to thereby provide the acicular body.

EXAMPLES

Examples are given below. Example 5 and 6 are reference examples.

Example 1

First, an acicular body original plate was formed in a silicon base using precision machine processing so that 64 circular cones (height: 120 μm, bottom diameter: 60 μm) in an 8×8 matrix were arrayed at an interval of 1 mm.

Then, a nickel film having a thickness of 500 μm was formed by plating on the acicular body original plate formed of the silicon base. The silicon base was then removed by wet-etching using a potassium hydroxide solution of 30 wt % concentration that has been heated to 90° C., thereby preparing an intaglio plate made of nickel.

Then, chitosan succinamide was dissolved in water to prepare an acicular body-forming liquid (viscosity: 0.01 Pa·s).

Then, the intaglio plate, as well as the acicular body-forming liquid in a container, was placed inside a vacuum chamber (desiccator) which was connected to a pump, followed by reducing pressure until a pressure environment of 0.01 MPa was created. The inner dimensions of the vacuum chamber (desiccator) were 18 cm×25.7 cm×26 cm. As the pump, a DTC-22 (ULVAC, Inc.) was used.

Then, the acicular body-forming solution was supplied to the intaglio plate under the reduced pressure environment of 0.01 MPa. As a method of supplying the acicular body-forming liquid to the intaglio plate, the vacuum chamber and the container were tilted to drip the acicular body-forming liquid from the opening of the container onto the intaglio plate. The time taken for creating the reduced pressure environment of 0.01 MPa was 1 minute and 28 seconds.

Then, the vacuum chamber was opened to the atmospheric air for return to the atmospheric pressure.

Then, the intaglio plate filled with the acicular body-forming liquid was heated under the atmospheric pressure at 40° C. for 60 minutes using a heat source to dry and solidify the acicular body-forming liquid, thereby obtaining an acicular body. As the heat source, a hot plate was used.

Then, the acicular body on the intaglio plate was punched into a circle with the Thomson blade.

Then, an adhesive member was attached to the back surface of the acicular body on the intaglio plate. As the adhesive member, one including an acrylic adhesive layer on a polyethylene terephthalate (PET) film was used.

Finally, the solidified acicular body was peeled from the intaglio plate, thereby obtaining an acicular body with an adhesive member.

Example 2

An acicular body was prepared in a manner similar to Example 1. However, at the supplying step, the pressure environment inside the vacuum chamber was set to 0.02 MPa. The time taken for obtaining the pressure environment of 0.02 MPa was 1 minute and 2 seconds.

Example 3

An acicular body was prepared in a manner similar to Example 1. However, at the supplying step, the pressure environment inside the vacuum chamber was set to 0.04 MPa. The time taken for obtaining the pressure environment of 0.04 MPa was 34 seconds.

Example 4

An acicular body was prepared in a manner similar to Example 1. However, at the supplying step, the pressure environment inside the vacuum chamber was set to 0.05 MPa. The time taken for obtaining the pressure environment of 0.05 MPa was 25 seconds.

Example 5

An acicular body was prepared in a manner similar to Example 1. However, at the supplying step, the pressure environment inside the vacuum chamber was set to 0.06 MPa. The time taken for obtaining the pressure environment of 0.06 MPa was 17 seconds.

Example 6

An acicular body was prepared in a manner similar to Example 1. However, at the supplying step, the pressure environment inside the vacuum chamber was set to 0.08 MPa. The time taken for obtaining the pressure environment of 0.08 MPa was 6 seconds.

<Confirmatory Experiment>

The acicular bodies of Examples 1 to 6 were confirmed visually and by means of a microscope. In the acicular bodies of Examples 1 to 4, appearances of the peaks of the circular cones serving as the tips of the protrusions were confirmed for all of the protrusions. It was confirmed that the acicular body-forming liquid of these examples was filled into the pointed bottom ends of the recesses of the intaglio plates. Meanwhile, in the acicular bodies of Examples 5 and 6, filling to the tips could not be confirmed in some of the protrusions of the acicular bodies.

Figure 10:
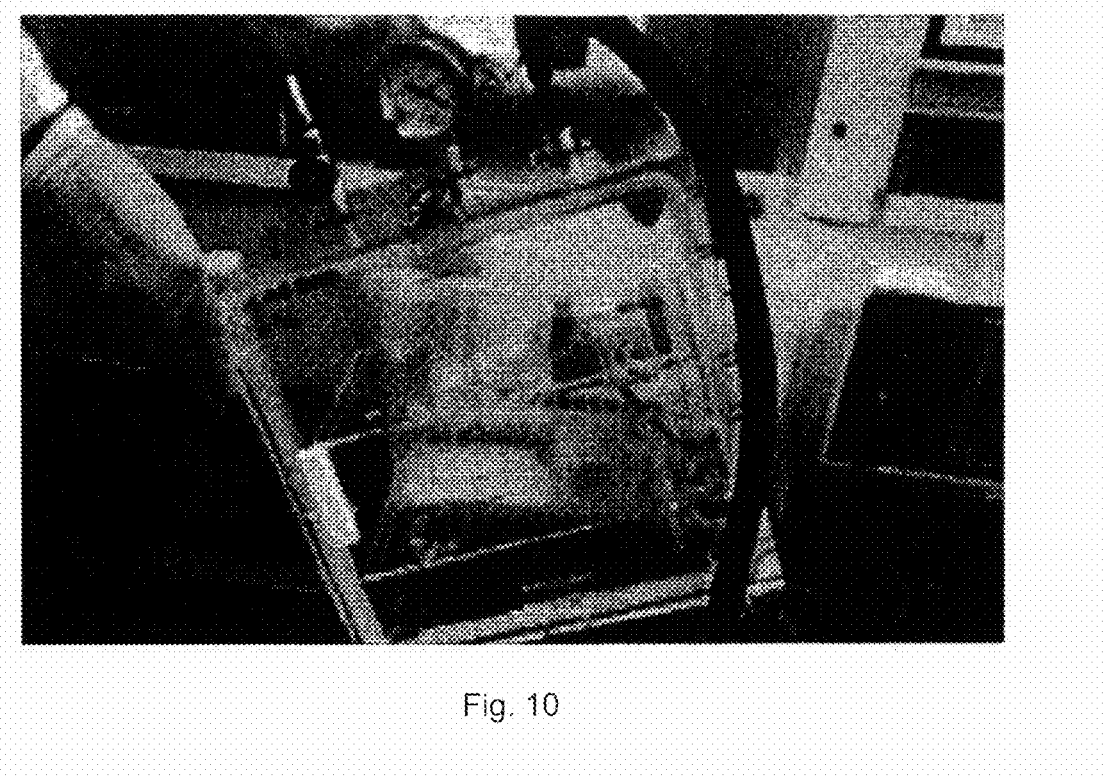
FIG. 10 is a photograph related to experiment of Examples 1 to 6.

FIG. 10 shows an experiment photograph of Examples 1 to 6. In Examples 1 to 6, the container (cup) containing the chitosan succinamide solution was secured inside the desiccator using a tape. After the reduced pressure environment was created, the desiccator was tilted to supply the chitosan succinamide solution to the intaglio plate.

Figure 11A:
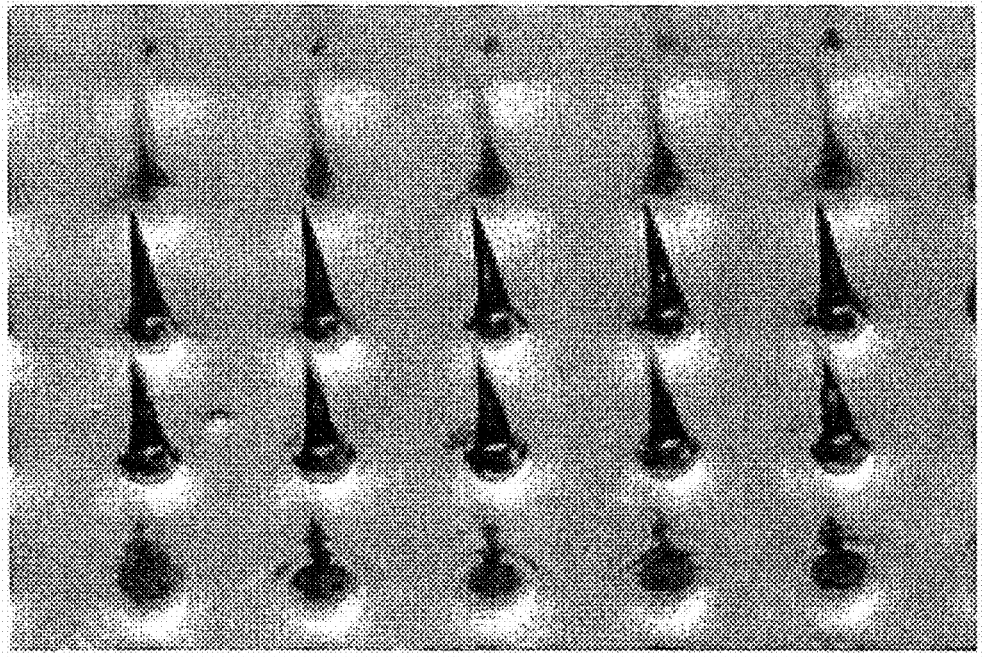
FIG. 11(a) shows a microscope photograph of an acicular body in Example 3.
Figure 11B:
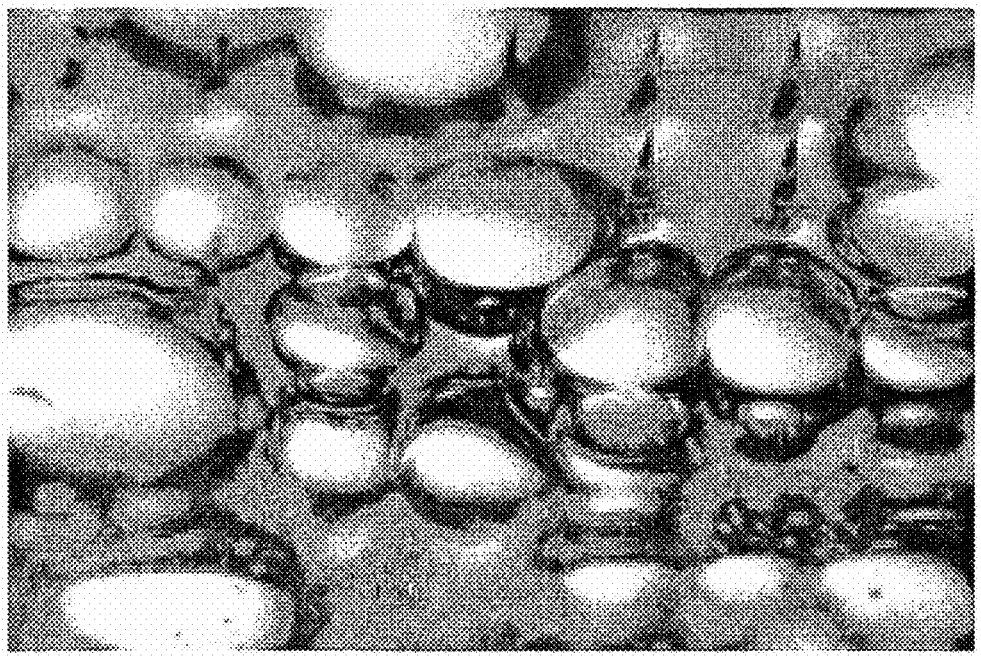
FIG. 11(b) shows a microscope photograph of an acicular body in Example 5.

FIG. 11(a) shows a microscope photograph of the acicular body in Example 3, and FIG. 11(b) shows a microscope photograph of the acicular body in Example 5. In the acicular body of Example 3, the formation of the circular conical protrusions was confirmed. Meanwhile, in the acicular body of Example 5, areas with no formation of the circular conical protrusions were confirmed.

Example 7

As the acicular body-forming liquid, a hydroxypropyl cellulose solution (viscosity: 0.08 Pa·s) was prepared. An intaglio plate similar to Example 1 was used. The intaglio plate was placed in a vacuum chamber, followed by reducing the pressure until a reduced pressure environment of 0.01 MPa was created.

Then, under the reduced pressure environment of 0.01 MPa, the acicular body-forming solution was supplied to the intaglio plate. As a method for supplying the acicular body-forming liquid to the intaglio plate, a dispenser was used. The nozzle of the dispenser was located inside the vacuum chamber, and the nozzle was connected, via a pipe, to a tank storing the acicular body-forming liquid and placed outside the vacuum chamber. The acicular body-forming liquid was dripped from the nozzle of the dispenser.

Then, the vacuum chamber was opened to the atmospheric air for return to the atmospheric pressure state.

Then, the intaglio plate filled with the acicular body-forming liquid was heated at 40° C. for 60 minutes using a hot plate to dry and solidify the acicular body-forming liquid, thereby forming an acicular body.

A tweezer was inserted between the intaglio plate and the acicular body to peel the acicular body from the intaglio plate, thereby obtaining the acicular body.

In the obtained acicular body, the circular conical protrusions could be confirmed. It was confirmed that the acicular body-forming liquid was filled into the pointed bottom ends of the recesses of the intaglio plate.

Example 8

As the acicular body-forming liquid, a pullulan solution (viscosity: 4 Pa·s) was prepared. An intaglio plate similar to Example 1 was used. The intaglio plate was placed in a vacuum chamber, followed by reducing the pressure until a reduced pressure environment of 0.01 MPa was created.

Then, under the reduced pressure environment of 0.01 MPa, the acicular body-forming solution was supplied to the intaglio plate. As a method for supplying the acicular body-forming liquid to the intaglio plate, a dispenser was used. The nozzle of the dispenser was located inside the vacuum chamber, and the nozzle was connected, via a pipe, to a tank storing the acicular body-forming liquid and placed outside the vacuum chamber. The acicular body-forming liquid was dripped from the nozzle of the dispenser.

Then, the vacuum chamber was opened to the atmospheric air for return to the atmospheric pressure state.

Then, the intaglio plate filled with the acicular body-forming liquid was heated at 70° C. for 240 minutes using a hot plate to dry and solidify the acicular body-forming liquid, thereby forming an acicular body.

A tweezer was inserted between the intaglio plate and the acicular body to peel the acicular body from the intaglio plate, thereby obtaining the acicular body.

In the obtained acicular body, the circular conical protrusions could be confirmed. It was confirmed that the acicular body-forming liquid was filled into the pointed bottom ends of the recesses of the intaglio plate.

Example 9

As the acicular body-forming liquid, a pectin solution (viscosity: 1 Pa·s) was prepared. An intaglio plate similar to Example 1 was used. The intaglio plate was placed in a vacuum chamber, followed by reducing the pressure until a reduced pressure environment of 0.01 MPa was created.

Then, under the reduced pressure environment of 0.01 MPa, the acicular body-forming solution was supplied to the intaglio plate. As a method for supplying the acicular body-forming liquid to the intaglio plate, a dispenser was used. The nozzle of the dispenser was located inside the vacuum chamber, and the nozzle was connected, via a pipe, to a tank storing the acicular body-forming liquid and placed outside the vacuum chamber. The acicular body-forming liquid was dripped from the nozzle of the dispenser.

Then, the vacuum chamber was opened to the atmospheric air for return to the atmospheric pressure state.

Then, the intaglio plate filled with the acicular body-forming liquid was heated at 80° C. for 240 minutes using a hot plate to dry and solidify the acicular body-forming liquid, thereby forming an acicular body.

A tweezer was inserted between the intaglio plate and the acicular body to peel the acicular body from the intaglio plate, thereby obtaining the acicular body.

In the obtained acicular body, the circular conical protrusions could be confirmed. It was confirmed that the acicular body-forming liquid was filled into the pointed bottom ends of the recesses of the intaglio plate.

An acicular body made of a biocompatible material that is a water-soluble polymer, such as chitosan, can dissolve inside the skin after piercing the skin. Thus, the acicular body may be prepared so as to contain a substance to be delivered into the skin, besides the water-soluble polymer. In this way, when the acicular body is pierced into the skin, the substance is delivered into the skin with the dissolution of the water-soluble polymer.

To prepare the acicular body using the water-soluble polymer material, some methods can be used including a method in which a water-soluble polymer material solution is cast in an acicular body intaglio plate, followed by drying, or a method in which the material is freeze-dried and solidified. There is another method of heating the material at a desired temperature to quicken drying. However, with this method, the air remaining in acicular body recesses of the intaglio plate expands, causing mixing of air bubbles in the solution filled in the intaglio plate. Thus, this method raises a problem that the acicular body is not filled with the solution to the tip end portions, or a problem that the air bubbles remain in the acicular body.

As a method of avoiding formation of air bubbles during heating and drying, as well as avoiding mixing of air bubbles in the acicular body, there is a method in which a material solution is supplied to the intaglio plate, followed by placing the plate in a reduced pressure environment. As a result, the air bubbles remaining in the recesses of the intaglio plate can be removed, and the recesses are filled with the material solution. Alternatively, the plate may be placed in a pressurized environment, instead of the reduced pressure environment, to remove the air bubbles from the recesses.

To remove the air bubbles from the recesses of the intaglio plate under a reduced pressure environment, the air bubbles are required to be moved to the top surface of the acicular body-forming liquid supplied to the top surfaces of the recesses. Therefore, when a high-viscosity material solution is used, the air bubbles are not easily released but, on the contrary, mixing of air bubbles in the acicular body may be accelerated. Furthermore, the air bubbles that are formed during pressure reduction may remain in the acicular body after the material is solidified.

When needle filling of the recesses is performed in a pressurized environment, the pressurization is required to be performed while controlling the pressurization speed so that the acicular body-forming liquid supplied to the recesses of the intaglio plate does not move from the desired supply location and the interface does not shake. Since this involves use of a pressurization chamber, a problem of increasing production cost is raised.

An object of the present invention is to provide a method for producing an acicular body that enables filling of a material solution to the pointed bottom ends of the recesses corresponding to respective protrusions.

To solve the above problems, the present invention provides a method for producing an acicular body provided with a support base and an acicular protrusion on one surface of the support base, characterized in that the method includes a supplying step of supplying an acicular body-forming liquid, in which an acicular body-forming material is dissolved or dispersed in a solvent, to an intaglio plate provided with a recess corresponding to a protrusion, under a pressure environment of not more than 0.05 MPa; a pressure changing step of changing a pressure environment of the acicular body-forming liquid supplied to the intaglio plate to a pressure higher than 0.05 MPa; a drying step of drying the acicular body-forming liquid supplied to the intaglio plate and forming an acicular body; and a peeling step of peeling the acicular body from the intaglio plate.

The method for producing an acicular body of the present invention enables producing an acicular body in which an acicular body-forming material is filled into the tips of the protrusions.

The acicular body of the present invention can be used in various fields requiring fine acicular bodies. For example, the present invention is expected to be applied to the acicular bodies used in MEMS devices, optical components, sample jigs, drug development, medical usages, cosmetics, and beauty usages, and the like.

REFERENCE SIGNS LIST 10 acicular body
11 protrusion
12 support base
21 acicular body
21' acicular body-forming liquid
22 intaglio plate
23 vacuum chamber
23a pump
24 hot plate
30a nozzle (dispenser)
30b pipe (dispenser)
30c tank (dispenser)
31 acicular body
31' acicular body-forming liquid
32 intaglio plate 33 vacuum chamber
33a pump
34 hot plate
35 Thomson blade
36 adhesive member
36a adhesive layer
36b base Obviously, numerous modifications and variations of the present invention are possible in light of the above teachings. It is therefore to be understood that within the scope of the appended claims, the invention may be practiced otherwise than as specifically described herein.

What is claimed is:

1. A method for producing an acicular body having a support base and an acicular protrusion on one surface of the support base, comprising:
   supplying an acicular body-forming liquid, in which an acicular body-forming material is dissolved or dispersed in a solvent, onto an intaglio plate having a recess corresponding to a protrusion, inside a chamber having a first pressure environment of not more than 0.05 MPa;
   introducing air into the chamber after the supplying such that the first pressure environment of the chamber is changed to a second pressure environment in a range of higher than 0.05 MPa to 0.08 MPa or less;
   drying the acicular body-forming liquid supplied to the intaglio plate under a pressure environment in a range of 0.04 MPa to 0.08 MPa such that the acicular body-forming liquid is solidified and that an acicular body is formed; and
   peeling the acicular body from the intaglio plate.

2. The method according to claim 1, wherein the acicular body-forming liquid supplied to the intaglio plate has a viscosity ranging from 0.01 Pa·s to 100 Pa·s.

3. The method according to claim 1, wherein the first pressure environment is changed to the second pressure environment such that a pressure change is within a range of 0.05 MPa to 0.08 MPa.

4. The method according to claim 1, wherein the air is introduced into the chamber such that the second pressure environment is 0.08 MPa.

5. The method according to claim 1, wherein the first pressure environment has a pressure ranging from 0.01 MPa to 0.05 MPa.

6. The method according to claim 1, wherein the drying is performed under the pressure environment of 0.04 MPa or 0.08 MPa.

7. The method according to claim 1, further comprising, after the drying:
   punching a peripheral edge portion of the acicular body in the intaglio plate; and
   attaching an adhesive member onto a surface of the acicular body from which the peripheral edge portion has been punched,
   wherein the peeling is performed after the attaching.

8. The method according to claim 1, wherein the acicular body-forming material comprises a water-soluble polymer or a polysaccharide.

9. The method according to claim 1, wherein the acicular body-forming material comprises at least one selected from the group consisting of chitosan, chitosan succinamide, hydroxypropyl cellulose, carboxymethyl cellulose, sodium chondroitin sulfate, curdlan, trehalose, sucrose, gelatin, collagen, pullulan, pectin, and alginate.

10. The method according to claim 1, wherein the acicular body-forming material comprises a drug or a cosmetic substance.

11. The method according to claim 1, wherein the solvent is water, and the drying is conducted at a heating temperature in a range of from 40° C. to 90° C.

12. The method according to claim 6, wherein the air is introduced into the chamber such that the second pressure environment is 0.08 MPa.

13. The method according to claim 12, further comprising:
   changing the second pressure environment to a pressure environment of not more than 0.05 MPa before the drying.

14. The method according to claim 12, further comprising:
   changing the second pressure environment to the first pressure environment before the drying.

15. The method according to claim 2, wherein the air is introduced into the chamber such that the second pressure environment is 0.08 MPa.

16. The method according to claim 15, further comprising:
   changing the second pressure environment to a pressure environment of not more than 0.05 MPa before the drying.

17. The method according to claim 15, further comprising:
   changing the second pressure environment to the first pressure environment before the drying.

18. The method according to claim 6, wherein the acicular body-forming liquid is supplied onto the intaglio plate inside the chamber having the first pressure environment of 0.04 MPa, and the air is introduced into the chamber such that the second pressure environment is 0.08 MPa.

19. The method according to claim 18, further comprising:
   changing the second pressure environment to a pressure environment of not more than 0.05 MPa before the drying.

20. The method according to claim 1, wherein the supplying includes transferring the acicular body-forming liquid from a container placed inside the chamber onto the intaglio pate.

* * * * *